US008332032B2

(12) United States Patent
Jackson et al.

(10) Patent No.: US 8,332,032 B2
(45) Date of Patent: Dec. 11, 2012

(54) HYBRID SINGLE-CHAMBER TO SIMULTANEOUS PACING METHOD FOR DISCRIMINATION OF TACHYCARDIAS

(75) Inventors: Troy E. Jackson, New Brighton, MN (US); Mark L. Brown, North Oaks, MN (US); Jeffrey M. Gillberg, Coon Rapids, MN (US)

(73) Assignee: Medtronic, Inc., Minneapolis, MN (US)

(*) Notice: Subject to any disclaimer, the term of this patent is extended or adjusted under 35 U.S.C. 154(b) by 386 days.

(21) Appl. No.: 12/358,280

(22) Filed: Jan. 23, 2009

(65) Prior Publication Data

US 2010/0191301 A1     Jul. 29, 2010

(51) Int. Cl.
*A61N 1/00* (2006.01)

(52) U.S. Cl. ............................................. 607/14; 607/4

(58) Field of Classification Search ................. 607/4, 14
See application file for complete search history.

(56) References Cited

U.S. PATENT DOCUMENTS

| | | | | |
|---|---|---|---|---|
| 5,117,824 | A | * | 6/1992 | Keimel et al. ..................... 607/4 |
| 5,411,530 | A | | 5/1995 | Akhtar |
| 5,545,186 | A | | 8/1996 | Olson et al. |
| 6,091,989 | A | * | 7/2000 | Swerdlow et al. ................ 607/5 |
| 6,393,316 | B1 | | 5/2002 | Gillberg |
| 7,162,300 | B2 | * | 1/2007 | van Groeningen et al. ..... 607/14 |
| 7,953,482 | B2 | * | 5/2011 | Hess ............................... 607/14 |
| 8,010,193 | B2 | * | 8/2011 | Saba ............................... 607/14 |
| 2001/0014816 | A1 | | 8/2001 | Hsu et al. |
| 2003/0191404 | A1 | | 10/2003 | Klein |
| 2004/0172067 | A1 | | 9/2004 | Saba |
| 2006/0217769 | A1 | | 9/2006 | Saba |
| 2008/0154322 | A1 | | 6/2008 | Jackson et al. |
| 2010/0324612 | A1 | * | 12/2010 | Matos ............................... 607/4 |

OTHER PUBLICATIONS

Daryl P. Ridley, Atrial Response to Ventricular Antitachycardia Pacing Discriminates Mechanism of 1:1 Atrioventricular Tachycardia, J cardiovasc Electrophysiol, vol. 16, pp. 601-605, Jun. 2005.
Samir Saba, Simultaneous Atrial and Ventricul Anti-Tachycardia Pacing as a novel Method of Rhythm Discrimination, J cardiovasc Electrophysiol, vol. 17, pp. 695-701, Jul. 2006.
P0025631.01 (PCT/US2010/020702) PCT Notification of Transmittal of the International Search Report and the Written Opinion of the International Searching Authority, Mailed Apr. 21, 2010, 8 pages.

* cited by examiner

*Primary Examiner* — Niketa Patel
*Assistant Examiner* — Catherine Voorhees
(74) *Attorney, Agent, or Firm* — Michael C. Soldner

(57) ABSTRACT

A cardiac medical device and associated method control delivery of anti-tachycardia pacing (ATP) in response to detecting tachycardia. In one embodiment, an initial set of single chamber pacing pulses are delivered in a single one of the atrium and the ventricle, the other one of the atrium and the ventricle being a non-paced chamber during the initial set of single chamber pacing pulses. The device detects simultaneity between a sensed event in the non-paced chamber and one of the single chamber pacing pulses and delivers ATP in both the atrium and the ventricle in response to detecting the simultaneity.

19 Claims, 5 Drawing Sheets

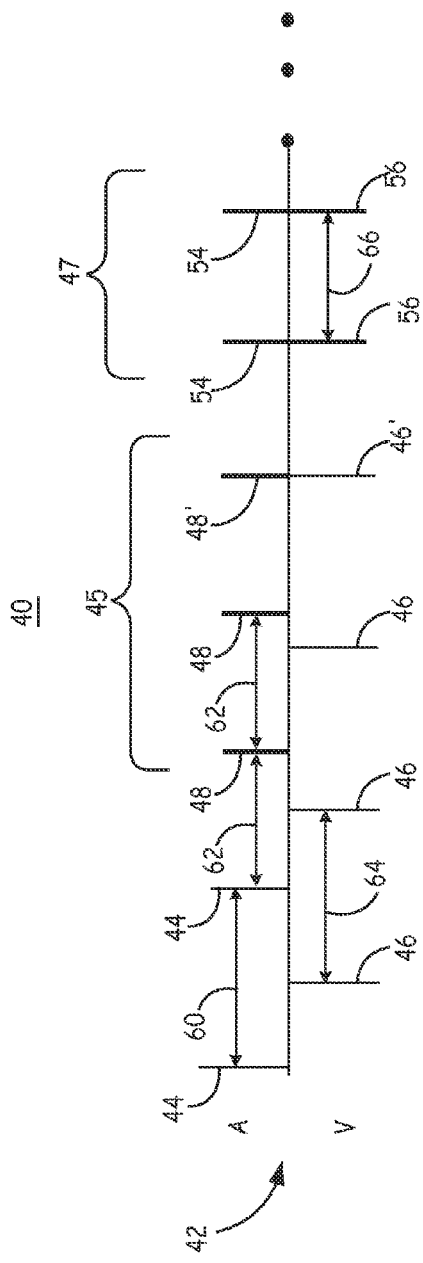
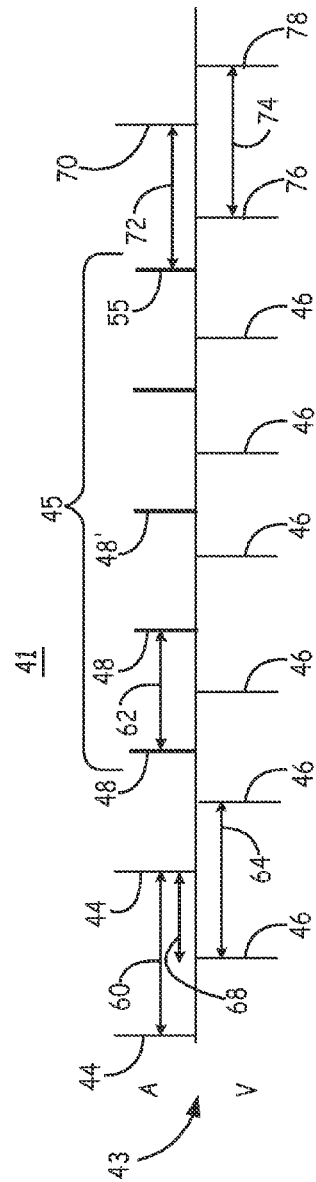
FIG. 3
FIG. 4

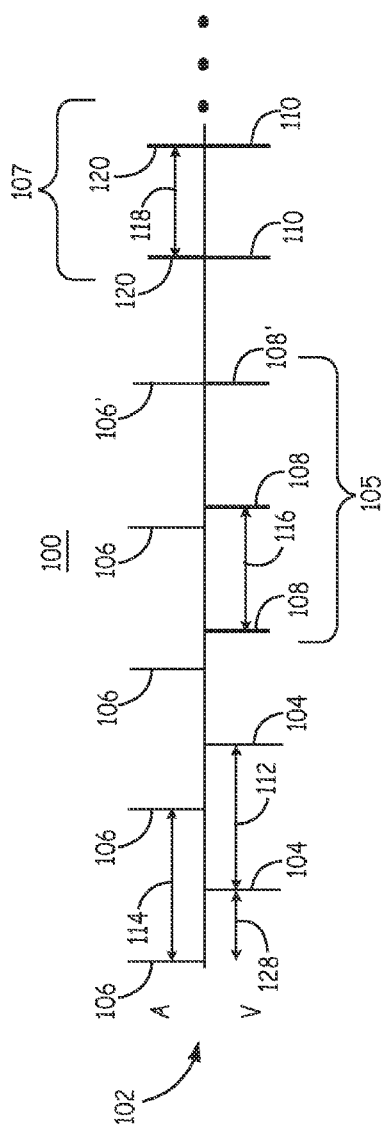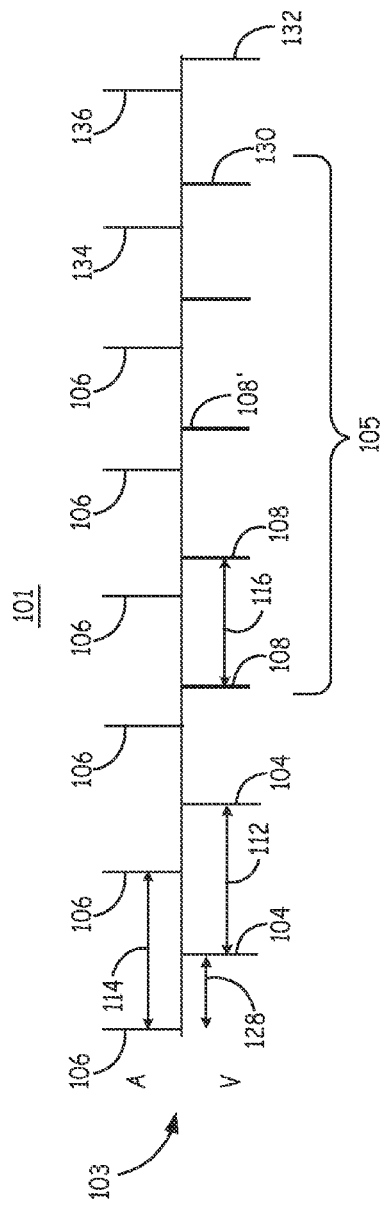

HYBRID SINGLE-CHAMBER TO SIMULTANEOUS PACING METHOD FOR DISCRIMINATION OF TACHYCARDIAS

TECHNICAL FIELD

The disclosure relates generally to cardiac medical devices and, in some embodiments, to a device and method for monitoring the heart rhythm and delivering therapy to the patient.

BACKGROUND

Cardiac medical devices can include diagnostic monitoring equipment, external medical device systems, and implantable medical devices (IMDs). Examples of IMDs include implantable hemodynamic monitors (IHMs), implantable cardioverter-defibrillators (ICDs), cardiac pacemakers, cardiac resynchronization therapy (CRT) pacing devices, and drug delivery devices.

ICDs are generally configured with one or more electrodes for sensing cardiac signals for monitoring the patient's heart rhythm. Upon interpreting one or more of the cardiac signals as arrhythmic, the ICD, in turn, can be used to deliver an appropriate therapy to the patient, with such therapies including pacing and/or defibrillation. Unfortunately, identifying the exact source of an arrhythmia can sometimes be a challenge to both automatic ICDs and the physicians taking care of patients with such ICDs.

For example, distinguishing between ventricular tachycardia (VT) and supraventricular tachycardia (SVT) can pose challenges. VT originates in the ventricular region of the heart, while SVT originates above the ventricular region of the heart, e.g., in the atrial region of the heart or the atrioventricular (AV) node. VT is considered the more severe cardiac event of the two for the patient.

One reason VT and SVT can be difficult to distinguish is that measured cardiac signals, for example an intracardiac electrogram (EGM) or a subcutaneous ECG signal, for each of these types of arrhythmias can be similar, and in turn, interpreted similarly by an ICD. When SVT occurs, the ICD may detect the fast ventricular rate as VT and deliver unneeded therapy to the ventricle. Such unneeded therapies, especially shock therapies, can be physically and emotionally distressful for patients and unnecessarily depletes the ICD battery.

SVT and VT are particularly difficult to distinguish from each other when SVT occurs with 1:1 antegrade conduction or when VT occurs with 1:1 retrograde conduction. In either of these situations, the ventricular and atrial rates will be equal making the two different rhythms appear similar on recorded cardiac signals.

In an attempt to minimize the occurrence of unneeded therapies, various algorithms to more effectively utilize the quantitative aspects of cardiac signals (e.g., EGM morphology, timing intervals between sensed R-waves and P-waves, patterns of sensed R-waves and P-waves, etc). Such evaluations of EGM signals have generally been found to have variable success. By implementing arrhythmia discrimination algorithms within ICDs, the incidence of unneeded therapy can be reduced from that of early generation ICDs. However, unneeded therapies can still occur.

What is needed are medical devices and systematic methods used to prevent the incidence of unneeded therapy, while also being adapted to limit other risks to the patient when using such devices and methods.

BRIEF DESCRIPTION OF THE DRAWINGS

FIG. 3 is a timing diagram illustrating a technique for delivering ATP in the atrial and ventricular regions of a patient's heart.

FIG. 4 is a timing diagram illustrating delivery of the ATP technique described in conjunction with FIG. 3 when simultaneity is not detected.

FIG. 5 is a timing diagram illustrating an ATP technique that includes delivering the initial set of single chamber pacing pulses in the ventricle rather than in the atrium.

FIG. 6 is a timing diagram illustrating the delivery of single chamber pacing pulses in the ventricle when simultaneity between a ventricular pacing pulse and an atrial sensed event does not occur.

DETAILED DESCRIPTION

Figure 1:
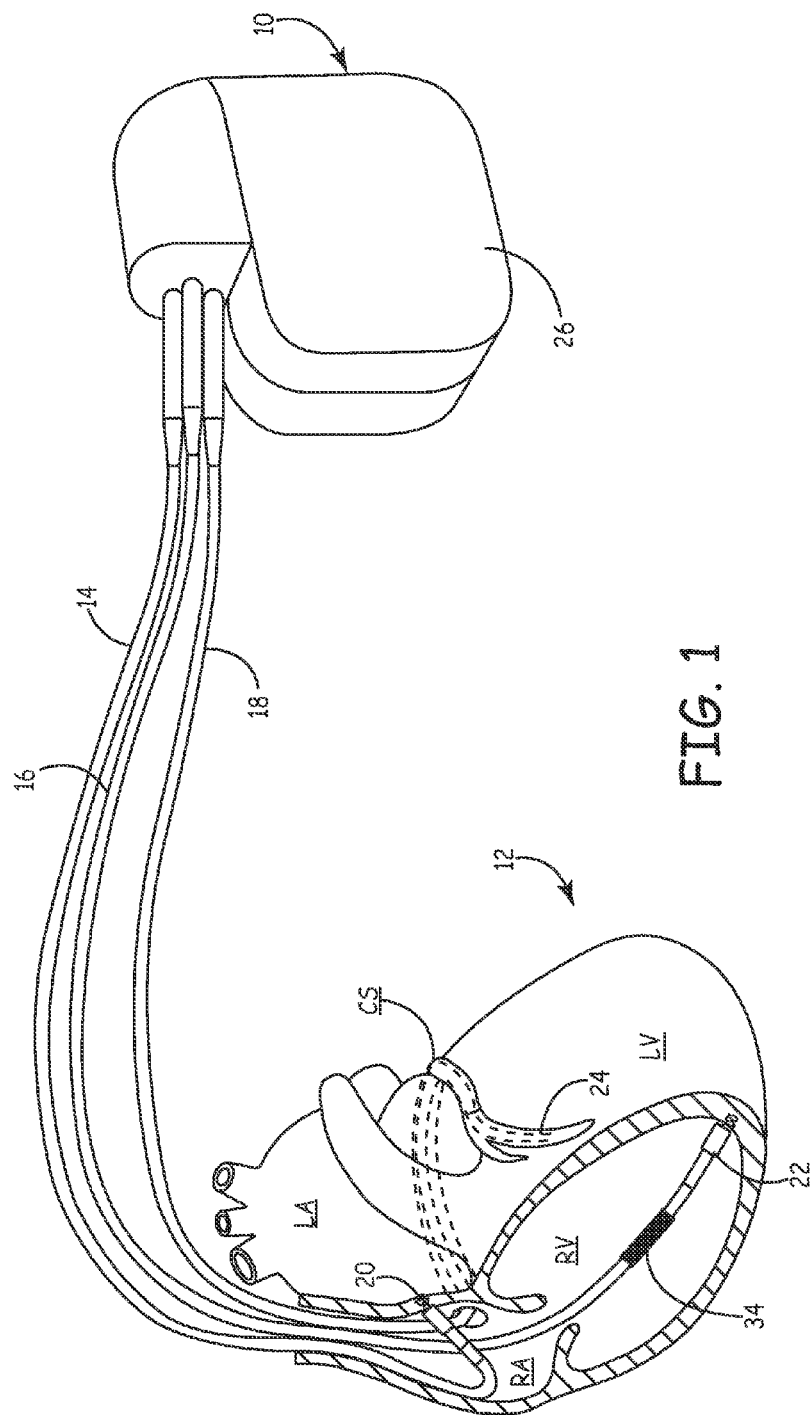
FIG. 1 shows a schematic representation of a cardiac medical device.

In the following description, references are made to illustrative embodiments. It is understood that other embodiments may be utilized without departing from the scope of the disclosure. For purposes of clarity, the identical reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

As described above, some methods used to distinguish VT from SVT in ICDs have involved using mathematical algorithms to more effectively utilize the quantitative aspects of the cardiac signals. However, as mentioned above, even when using such methods, discrimination between SVT and VT remains a challenge.

A recent technique to distinguish VT from SVT is generally described in U.S. patent application Ser. No. 10/717,248, now issued as U.S. Pat. No. 7,206,633 (Saba), hereby incorporated herein by reference in relevant part. Briefly, the earliest arriving electrical signal sensed following simultaneous pacing in the atria and in the ventricle is used to diagnose the tachycardia as SVT or VT based.

While the simultaneous pacing technique can be used in ICDs to effectively differentiate between arrhythmias originating in the ventricular and supraventricular regions of the heart, it has been found, at times, to also create conditions that are atrial proarrhythmic. The simultaneous pacing can result in atrial pacing pulses falling during the atrial vulnerable period with the potential to induce atrial tachyarrhythmia, e.g., atrial fibrillation or atrial flutter, in some patients.

Embodiments described herein include the use of atrial and ventricular paced pulses that are synchronized so as to be delivered in a simultaneous manner. However, in certain embodiments, delivery of simultaneous atrial and ventricular pacing pulses is provided in a gradual manner with reduced potential of inducing atrial arrhythmia. As illustrated below, upon sensing actual or suspected tachycardia in both the atrial and ventricular regions, pacing is initiated using single chamber pacing delivered to either the atrial or the ventricular regions but not both. The single chamber pacing is delivered at a rate to sufficiently overdrive the corresponding atrial or ventricular chamber. Sensing of intrinsic events in the non-paced chamber continues during the single chamber pacing. Upon sensing an intrinsic event in the non-paced chamber that is substantially simultaneous with one of the single chamber pacing pulses delivered in the paced chamber, simultaneous dual chamber pacing is initiated. This technique allows simultaneous pacing of the atria and the ventricles to be achieved with a reduced risk of proarrhythmia.

FIG. 1 shows a schematic representation of a cardiac medical device 10. Cardiac medical device 10 is embodied as an ICD in FIG. 1, however, embodiments described herein should not be interpreted as being limited to any particular implantable medical device or any particular cardiac medical device. Instead, embodiments may include any cardiac medical device so long as the device utilizes a plurality of electrodes or other sensors for monitoring the cardiac rhythm of a patient and for delivering pacing pulses to the patient. The electrodes are capable of sensing cardiac EGM or ECG signals, referred to herein collectively as "cardiac signals" in the upper atrial chambers and in the lower ventricular chambers.

In FIG. 1, heart 12 includes the right atrium (RA), left atrium (LA), right ventricle (RV), left ventricle (LV), and the coronary sinus (CS) extending from the opening in the right atrium to form the great cardiac vein. FIG. 1 depicts the medical device 10 in relation to the heart 12. In certain embodiments, the medical device 10 can be an implantable, multi-channel ICD. As shown, three transvenous leads 14, 16, and 18 connect the medical device 10 with the RA, the RV and the LV, respectively. Each lead includes at least one electrical conductor and pace/sense electrode. For example, leads 14, 16 and 18 are respectively connected to pace/sense electrodes 20, 22, and 24. In addition, a can electrode 26 can be formed as part of the outer surface of the housing of the medical device 10. The pace/sense electrodes 20, 22, and 24 and can electrode 26 can be selectively employed to provide a number of unipolar and bipolar pace/sense electrode combinations for pacing and sensing functions. The depicted positions in or about the right and left heart chambers are merely illustrative. Moreover, other leads and pace/sense electrodes can be used instead of, or in combination with, any one or more of the depicted leads and electrodes.

Typically, in pacing systems of the type illustrated in FIG. 1, the electrodes designated herein as "pace/sense" electrodes are used for both pacing and sensing functions. In certain embodiments, these electrodes can be used exclusively as pace or sense electrodes in programmed or default combinations for sensing cardiac signals and delivering pace pulses.

A coil electrode 34 is also shown as being coupled to a portion of RV lead 16. Coil electrodes can additionally or alternatively be coupled to portions of any of the leads of FIG. 1, such as LV lead 18. The coil electrode 34, or other similar electrode types can be electrically coupled to low voltage circuitry for delivering low voltage pacing pulses in addition to high voltage circuitry for delivering high voltage cardioversion/defibrillation shock pulses. Electrodes shown in FIG. 1 can be disposed in a variety of locations in, around, and on the heart.

The leads and electrodes described above can be employed to record cardiac signals in the atria and the ventricles. The recorded data can be periodically transmitted to a programmer or other external device enabled for telemetric communication with the medical device 10.

Figure 2:
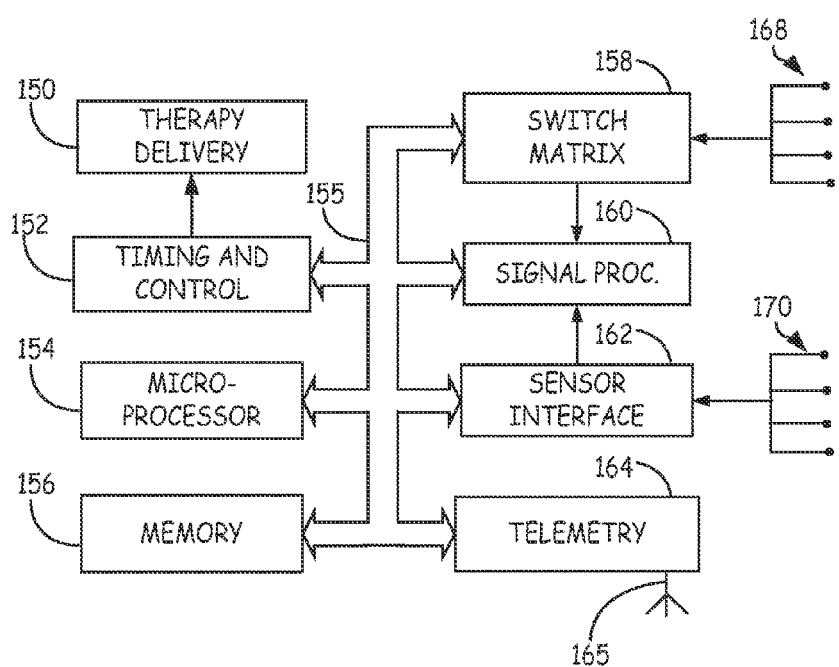
FIG. 2 is a functional block diagram of the implantable cardiac medical device shown in FIG. 1 according to one embodiment.

FIG. 2 is a functional block diagram of implantable cardiac medical device 10 shown in FIG. 1 according to one embodiment. Cardiac medical device 10, referred to hereafter as ICD 10, generally includes timing and control circuitry 152 and a controller that may be embodied as a microprocessor 154 or a digital state machine for timing sensing and therapy delivery functions in accordance with a programmed operating mode. Microprocessor 154 and associated memory 156 are coupled to the various components of ICD 10 via a data/address bus 155. ICD 10 includes therapy delivery unit 150 for delivering electrical stimulation therapies, such as cardiac pacing therapies and arrhythmia therapies such as anti-tachycardia pacing (ATP) and cardioversion/defibrillation shocks, under the control of timing and control 152 and microprocessor 154. Therapy delivery unit 150 is typically coupled to two or more electrodes 168 via an optional switch matrix 158. Switch matrix 158 is used for selecting which electrodes and corresponding polarities are used for delivering electrical stimulation pulses.

Cardiac electrical signals are sensed for determining when an electrical stimulation therapy is needed and in controlling a stimulation mode and the timing of stimulation pulses. Electrodes used for sensing and electrodes used for stimulation may be selected via switch matrix 158. When used for sensing, cardiac signals received by electrodes 168 are coupled to signal processing circuitry 160 via switch matrix 158. Signal processor 160 includes sense amplifiers and may include other signal conditioning circuitry such as filters and an analog to digital converter. Cardiac electrical signals may then be used by microprocessor 154 for detecting physiological events, such as detecting and discriminating cardiac arrhythmias. Signal processing circuitry 160 may include event detection circuitry generally corresponding to P-wave or R-wave detection circuitry as disclosed in U.S. Pat. No. 5,117,824 (Keimel, et al.), hereby incorporated herein by reference in its entirety.

Arrhythmia detection algorithms may be implemented for detecting ventricular tachycardia (VT), ventricular fibrillation (VF) as well as atrial arrhythmias such as atrial fibrillation (A FIB). Sensed ventricular event intervals (R-R intervals) measured from the sensed cardiac signals are commonly used for detecting ventricular arrhythmias. Likewise, sensed atrial event intervals (P-P intervals) measured from sensed cardiac signals are commonly used for detecting atrial arrhythmias. Additional information obtained such as R-wave morphology, slew rate, other event intervals (e.g., P-R intervals) or other sensor signal information may be used in detecting, confirming or discriminating an arrhythmia. Reference is made, for example, to U.S. Pat. No. 5,354,316 (Keimel), U.S. Pat. No. 5,545,186 (Olson et al.) and U.S. Pat. No. 6,393,316 (Gillberg et al.) for examples of arrhythmia detection and discrimination using EGM signals and the provision of arrhythmia therapies in response to arrhythmia detection and discrimination, all of which patents are incorporated herein by reference in their entirety.

In one detection scheme, programmable detection interval ranges designate the range of sensed event intervals indicative of a tachycardia and may be defined separately for detecting slow tachycardia, fast tachycardia and fibrillation. In addition to event interval information, the morphology of the EGM signal may be used in discriminating heart rhythms. As will be described herein, the cardiac signal response to ATP initiated in response to detecting both atrial and ventricular tachycardias can be used to discriminate between SVT and VT. ICD microprocessor 154 may initiate ATP for use in tachycardia discrimination particularly when the sensed atrial and ventricular tachycardia rates are so similar that other tachycardia detection methods are not sensitive enough to discriminate between VT and SVT.

In response to an arrhythmia detection, a programmed arrhythmia therapy is delivered by therapy delivery module 150 under the control of timing and control 152. A description of high-voltage output circuitry and control of high-voltage shock pulse delivery is provided in the above-incorporated '186 Olson patent.

ICD 10 may additionally be coupled to one or more physiological sensors 170. Physiological sensors 170 may include pressure sensors, accelerometers, flow sensors, blood chemistry sensors, activity sensors or other physiological sensors known for use with implantable cardiac stimulation devices. Physiological sensors may be carried by leads extending from ICD 10 or incorporated in or on the ICD housing.

Signals from sensors 170 are received by a sensor interface 162 which provides sensor signals to signal processing circuitry 160. Sensor signals are used by microprocessor 154 for detecting physiological events or conditions. For example, ICD 10 may monitor heart wall motion, blood pressure, blood chemistry, respiration, or patient activity or posture. Monitored signals may be used for sensing the need for delivering a therapy under control of the operating system.

The operating system includes associated memory 156 for storing a variety of programmed-in operating mode and parameter values that are used by microprocessor 154. The memory 156 may also be used for storing data compiled from sensed physiological signals and/or relating to device operating history for telemetry out on receipt of a retrieval or interrogation instruction. ATP delivery parameters and tachycardia discrimination rules and algorithms may be stored in memory 156 and utilized by microprocessor 154 for controlling the delivery of ATP and discriminating detected tachycardia episodes. In one embodiment, memory 156 stores a set of tachycardia discrimination rules relating to a heart's response to dual chamber ATP and a set of tachycardia discrimination rules relating to a heart's response to single chamber ATP.

As will be described in greater detail herein, microprocessor 154 selects a stored set of tachycardia discrimination rules to be applied for discriminating a detected tachycardia. The rules are selected in response to detecting simultaneity between a single chamber ATP pulse and a sensed event in a non-paced chamber following tachycardia detection. When such simultaneity is detected, the microprocessor 154 will cause timing and control 152 to enable therapy delivery 150 to deliver simultaneous ATP in both the atria and the ventricles. Tachycardia discrimination rules relating to the heart's response to dual chamber ATP will be selected and applied by microprocessor 154 for discriminating the detected tachycardia as SVT or VT. When such simultaneity is not detected, the microprocessor 154 will withhold dual chamber ATP delivery and complete delivery of a set of single chamber ATP pulses. Tachycardia discrimination rules relating to the heart's response to single chamber ATP will be selected and applied for discriminating the detected tachycardia.

ICD 10 further includes telemetry circuitry 164 and antenna 165. Programming commands or data are transmitted during uplink or downlink telemetry between ICD telemetry circuitry 164 and external telemetry circuitry included in a programmer or monitoring unit.

FIG. 3 is a timing diagram 40 illustrating a technique used by the ICD 10 of FIG. 1 for delivering ATP in the atrial and ventricular regions of a patient's heart. As used herein, "single chamber pacing" refers to pacing delivered to only one of the atrial region or the ventricular region but not both the atrial and ventricular regions. As such, "single chamber" pacing pulses may be delivered in one or both atria or generally any atrial region. Alternatively "single chamber" pacing pulses may be delivered in one or both ventricles or generally any ventricular region. However, during single chamber pacing, only the upper atrial chamber(s) are paced or only the lower ventricular chamber(s) are paced but not both the atria and the ventricles. As used herein, "dual chamber" pacing refers to pacing delivered in both atrial and ventricular regions. Dual chamber pacing pulses are delivered in one or both atria and in one or both ventricles. The interval between an atrial pacing pulse and a ventricular pacing pulse is referred to as the atrial-ventricular pacing interval (AVI).

Pacing techniques described herein are provided via a controller within the IMD 10, such as the microprocessor 154 operating in conjunction with memory 156 and timing and control module 152 in FIG. 2. A controller may alternatively be implemented using one or more digital state machines. A controller providing the functionality described herein may include functionality distributed across more than one cardiac medical device component.

The timing diagram 40 of FIG. 3 includes a timeline 42, showing sensing and pacing of a patient's atrium (A) on the upper portion of the timeline 42 and sensing and pacing of a patient's ventricle (V) on the lower portion of the timeline 42. The sensed and paced atrium can involve either or both of the patient's atria and likewise, the sensed and paced ventricle can involve either or both of the patient's ventricles.

Atrial sensed (Asense) events 44 are sensed using at least one sensing electrode positioned in operative relation to an atrial chamber and electrically coupled to the ICD 10. Asense events 44 represent the detection of a P-wave of an atrial signal. The sensed P-wave corresponds to the intrinsic depolarization of atrial tissue as opposed to an evoked depolarization of the atrial tissue caused by an atrial pacing pulse. Atrial pacing pulses (Apace pulses), e.g. atrial pacing pulse 48, are delivered via at least one electrode coupled to the IMD 10 and positioned to evoke depolarization of atrial tissue. An electrode used to sense events 44 and to deliver pacing pulses 48 may be the same electrode.

Ventricular sense (Vsense) events 46 are sensed using at least one sensing electrode positioned in operative relation to a ventricular chamber and electrically coupled to the ICD 10. Vsense events 46 represent the detection of an R-wave of a ventricular signal. The sensed R-wave corresponds to an intrinsic depolarization of ventricular tissue as opposed to an evoked depolarization caused by a ventricular pacing pulse. Ventricular pacing pulses 56 are delivered via one or more electrodes coupled to the ICD 10 and positioned to evoke depolarization of the ventricular tissue.

Generally speaking, Asense events 44 and Vsense events 46 may be the result of purely intrinsic activation of the myocardial tissue or intrinsically conducted depolarizations arising from an evoked depolarization response to a pacing pulse delivered in another heart chamber. In other words, an Asense event may be an atrial depolarization conducted from the ventricles when a ventricular pacing pulse causes an evoked response in the ventricles. A Vsense event may be a ventricular depolarization conducted from the atria after an atrial pacing pulse causes an evoked response in the atria.

The initial cycle length 60 of Asense events 44 and cycle length 64 of Vsense events 46 are each interpreted as meeting tachycardia detection criteria. In accordance with one embodiment, when tachycardia detection criteria are satisfied in both the atria and the ventricles, an ATP regime is initiated. However, in contrast to past techniques that involve immediately delivering ATP in both atrial and ventricular chambers in response to detecting tachycardia in both chambers, ATP is initially delivered as a set of single-chamber pacing pulses 45 that are followed by a set of dual chamber pacing pulses 47 after detecting simultaneity of a single chamber pacing pulse and a sensed event in the non-paced chamber.

The ATP regimes described herein and illustrated in FIGS. 3 through 6 are generally provided when an atrial tachycardia rate corresponding to atrial cycle length 60 and a ventricular tachycardia rate corresponding to ventricular cycle length 64 are substantially equal. For example, atrial cycle length 60 and ventricular cycle length 64 may be within 30 ms of each other to be determined to be substantially equal. The detection of substantially equal cycle lengths or substantially equal atrial and ventricular tachycardia rates may be implemented according to other criteria in varying embodiments, which may require a cycle length difference of less than some maximum value which may be more or less than the example of a maximum 30 ms difference. The atrial cycle length 60 and the ventricular cycle length 64, being substantially equal, are also referred to herein as the "tachycardia cycle length".

ATP delivered according to illustrative embodiments described herein may serve as an initial method of treating the tachycardia. However, even if the ATP fails to terminate the tachycardia, the ATP can be used to identify the source of the tachycardia to prompt additional, yet more appropriate, therapy to be delivered in treating the patient.

In FIG. 3, an initial set of single chamber pacing pulses 45 are delivered in the atrium at an atrial pacing cycle length (ACL) 62 shorter than the tachycardia cycle length 60 so as to overdrive the atrium. Apace pulses 48 are delivered at the ACL 62 set to avoid delivery of the Apace pulses 48 during the atrium's vulnerable period.

Depending on the type of arrhythmia present, a ventricular sense event 46' may occur simultaneously with one of the single chamber Apace pulses 48'. Upon detecting simultaneity between an Apace pulse 48' and a Vsense event 46', the controller switches the ATP from single chamber pacing 45 to simultaneous dual chamber pacing 47. Simultaneity of the Vsense event 46' and the Apace pulse 48' is detected when the Vsense event 46' occurs within a predetermined time interval around the Apace pulse 48'.

In one embodiment, simultaneity between a sensed event in the non-paced chamber (the ventricle in this example) and one of the single chamber pacing pulses is detected when the sensed event 46' occurs within a predetermined time interval of the single chamber pacing pulse 48'. In another embodiment, simultaneity is detected when the sensed event in the non-paced chamber is within the difference between the pacing cycle length and the tachycardia cycle length of the non-paced chamber. For example if the pacing cycle length is set to be 20 ms shorter than the tachycardia cycle length, simultaneity is detected when the sensed event occurs within 20 ms of the pacing pulse.

Upon detecting simultaneity, the ATP regime terminates the set of single chamber pacing pulses 45 and initiates a next set of ATP pulses 47 delivered as dual chamber pacing pulses 54 and 56 in both of the atrium and the ventricle, respectively. In one embodiment the dual chamber pacing 47 is started immediately upon detecting simultaneity. In other words, the single chamber pacing pulse 48,' with which a simultaneous Vsense event 46' occurred, is directly followed by an atrial pacing pulse 54 delivered simultaneously with a ventricular pacing pulse 56. No intervening single chamber Apace pulses 48 or Asense events 48 occur between the detection of simultaneity and the onset of dual chamber pacing 47.

During the dual chamber pacing 47 of the ATP regime, Vpace pulses 56 are delivered simultaneously with atrial pacing pulses 54, i.e. at an AVI of 0 ms or another fixed value. The Vpace pulses 56 are thus delivered at a ventricular pacing cycle length 66 equal to the atrial pacing cycle length 62. In this way, simultaneous atrial and ventricular pacing at an overdrive pacing rate is achieved while avoiding delivery of Apace pulses 48 or 54 during the atrium's vulnerable period. The likelihood of atrial proarrhythmia is reduced using this technique of gradually achieving simultaneous dual chamber ATP.

The set of dual chamber simultaneous pacing pulses 47 may include a specified number of pacing pulses after which an analysis of the first intrinsic event sensed after pacing termination allows discrimination of SVT and VT as generally described in the '248 patent application. Briefly, if a Vsense event occurs prior to an Asense event after termination of the dual chamber simultaneous pacing 47, the tachycardia is discriminated as VT, i.e., originating in the ventricles. If an Asense event is sensed first, prior to a Vsense event, after termination of the dual chamber simultaneous pacing 47, the tachycardia is discriminated as SVT. If an Asense and Vsense occur simultaneously, the arrhythmia is discriminated as a supraventricular tachycardia known as atrio-ventricular nodal re-entrant tachycardia. Accurate discrimination of the detected tachycardia allows appropriate therapy decisions to be made by the ICD.

FIG. 4 is a timing diagram 41 illustrating delivery of the ATP technique described in conjunction with FIG. 3 when simultaneity is not detected. Atrial events are shown along the top portion of timeline 43 and ventricular events are shown along the bottom portion of timeline 43. Asense events 44 occur at a cycle length 60 meeting atrial tachycardia detection criteria, and Vsense events 46 occur at a cycle length 64 meeting ventricular tachycardia detection criteria. In response to the tachycardia detection in both atrial and ventricular chambers, having similar cycle lengths 60 and 64, the ICD controller initiates ATP with a set of single chamber atrial pacing pulses 45 at an atrial pacing cycle length 62 shorter than the tachycardia cycle length 60. The single chamber atrial pacing pulses 45 are thus delivered at a rate faster than the rate of the detected tachycardia.

As observed in FIG. 4, Vsense events 46 continue without occurring simultaneously with Apace pulses 48. Apace pulse 48' represents an atrial pacing pulse upon which simultaneity is expected to occur. In some embodiments, the number of pacing pulses included in the initial set of single-chamber pacing pulses 45 is set by the ICD controller based on an expected number of pacing pulses required to reach simultaneity between a pacing pulse and a sensed event in the non-paced chamber. The ICD controller may compute the expected number of single chamber pacing pulses required to reach simultaneity using the measured tachycardia cycle length and the selected single chamber pacing cycle interval.

In one embodiment, the expected number of required pulses, Nexp, is computed as:

$$N\text{exp} = \text{FLOOR}\{VA_o/(TCL-ACL)\}+1 \quad (1)$$

wherein "$VA_o$" is the intrinsic ventricular-atrial interval 68 occurring between a Vsense event 46 and an Asense event 44, "TCL" is the tachycardia cycle length (measured as the atrial cycle length 60 or the ventricular cycle length 64, which are substantially equal), and "ACL" is the atrial pacing cycle length 62. The $VA_o$ interval divided by the difference between the TCL and the ACL indicates the number of pacing cycles required for the $VA_o$ interval to be reduced to near simultaneous atrial pace and ventricular sense events. The "FLOOR" function produces an integer value for the expected number of cycles by rounding down the result of the bracketed portion of equation 1. The expected number of cycles plus one gives the expected number of pacing pulses to reach simultaneity.

Each of the $VA_o$ and ACL terms in Equation 1 can be expressed as a percentage of the tachycardia cycle length (TCL) 64. For example, if $VA_o$ is approximately 40% of the TCL and the ACL is selected to be 80% of the TCL to overdrive pace the atrium, $$N\text{exp} = \text{FLOOR}\{0.4/(1-0.8)\}+1=3$$

As seen in FIG. 3, simultaneity of a Vsense event 46' and the third pacing pulse, Apace pulse 48', occurs as predicted based on the example computation of Nexp given above.

In FIG. 4, simultaneity does not occur. The total number of pacing pulses delivered during the initial set of single chamber pulses 45 may be set based on the computed Nexp. For example, a set of Nexp+n pacing pulses may be delivered to allow simultaneity to occur. If simultaneity is not detected during the total number of pacing pulses, the controller can analyze atrial and ventricular event patterns and intervals (e.g., AA intervals, VV intervals, and AV intervals) during and/or immediately following the single chamber pacing for tachycardia discrimination purposes.

Analysis of atrial and ventricular intervals during or after single chamber pacing for tachycardia discrimination purposes may correspond to the methods generally disclosed in U.S. Pat. No. 5,411,530 (Akhtar) or U.S. patent application Ser. No. 10/117,187 (Klein, U.S. Publication No. 2003/0191404), both of which patent documents are incorporated herein by reference in their entirety.

In one embodiment, a tachyarrhythmia discrimination analysis may include evaluating the first AA cycle length 72 measured between the last atrial pulse 55 and the first Asense event 70 after termination of atrial pacing. The analysis may further include evaluating the first VV cycle length 74 occurring between the last Vsense event 76 following the last atrial pulse 55 and the next Vsense event 78. If the AA cycle length 72 is greater than or equal to the original tachycardia cycle length 60, then the tachycardia is detected as SVT. Additional criteria may be applied for detecting SVT. For example, SVT is not detected if an intervening Vsense event is detected after Vsense event 76 and before the first Asense event 70 (resulting in a VVA pattern after termination of single chamber pacing). Detecting a VVA pattern would be evidence of VT. Another tachycardia discrimination rule may require the first ventricular cycle length 74 to be greater than the first atrial cycle length 72 after the last pacing pulse 55 in order to detect SVT. The post-ATP AA cycle length 72 and subsequent AA cycle lengths (not shown) may be further analyzed to determine if the tachycardia has been terminated by the atrial pacing or if the tachycardia is sustained.

FIG. 5 is a timing diagram 100 illustrating an ATP technique that includes delivering the initial set of single chamber pacing pulses in the ventricle rather than in the atrium. Asense events 106 and Vsense events 104 are shown on timeline 102 occurring at cycle lengths 114 and 112, respectively, each meeting tachycardia detection criteria. When intervals 112 and 114 are substantially equal, the origin of the tachycardia is indeterminable from the atrial and ventricular tachycardia rates alone. As such, an ATP regime is initiated with a set 105 of single chamber pacing pulses 108 delivered in the ventricle at a pacing interval 116 less than the tachycardia cycle interval 112 to overdrive pace the ventricles.

An Asense event 106' occurs substantially simultaneously with the third pacing pulse 108'. Upon detecting simultaneity of the Asense event 106' with a pacing pulse 108', the ATP regime converts to dual chamber pacing 107. Dual chamber pacing pulses 107 include atrial pacing pulses 120 delivered simultaneously with ventricular pacing pulses 110, i.e., at a 0 ms AVI, and an atrial pacing interval 118 equal to ventricular pacing interval 116. Simultaneous dual chamber pacing 107 may continue for a predetermined number of pacing pulses. Upon termination of dual chamber pacing, tachycardia discrimination analysis may be performed based on the first sensed event, atrial or ventricular, following ATP termination as described previously.

FIG. 6 is a timing diagram 101 illustrating the delivery of single chamber pacing pulses in the ventricle when simultaneity between a Vpace pulse and an Asense event does not occur. Asense events 106 at an atrial tachycardia cycle length 114 are shown on the upper portion of timeline 103. Vsense events 104 occurring at a ventricular tachycardia cycle length 112 are shown along the bottom portion of timeline 103. The atrial cycle length 114 and the ventricular cycle length 112 are approximately equal so that the tachycardia is indiscriminate based on the tachycardia cycle lengths.

Single chamber ventricular pacing pulses 108 are delivered at a pacing cycle length 116 which is less than tachycardia cycle length 112. As generally described above, an expected number of pacing pulses required to reach simultaneity between a pacing pulse and a sensed event in the non-paced chamber can be computed. The ICD controller sets a maximum number of pacing pulses 108 in the initial set of single chamber pacing pulses 105 in response to the computed expected number of single chamber pacing pulses required to reach simultaneity.

In the case of ventricular single chamber pacing, the expected number of pulses Nexp is computed using the intrinsic AV interval 128 to determine how many pacing pulses are required for an Asense to occur simultaneously with a ventricular pacing pulse:

$$N\text{exp}=\text{FLOOR}\{AV_o/(TCL-VCL)\}+1$$

The $AV_o$ interval 128 divided by the difference between the TCL 114 and the ventricular pacing cycle length (VCL) 116 indicates the number of pacing cycles required for the $AV_o$ interval to be reduced to near simultaneous atrial pace and ventricular sense events. The "FLOOR" function produces an integer value for the expected number of cycles, and adding one gives the expected number of pacing pulses to reach simultaneity.

A set of Nexp+n pacing pulses may be delivered to allow simultaneity to occur, and if simultaneity does not occur, the Nexp+n pulses allows analysis of atrial and ventricular patterns and/or intervals for tachycardia discrimination purposes during and/or immediately following the single chamber pacing.

In FIG. 6, simultaneity does not occur upon the expected pacing pulse 108'. The ICD controller delivers a predetermined maximum number of pacing pulses during single chamber pacing 105. Simultaneity is not detected during single chamber pacing 105. The ICD controller withholds the next set of dual chamber pacing pulses in response to delivering the maximum number of single chamber pacing pulses without detecting simultaneity between a sensed event 106 in the non-paced chamber and one of the single chamber pacing pulses 108 or 130.

In accordance with one embodiment, the ICD controller selects tachycardia discrimination rules to be applied for discriminating the detected tachycardia in response to whether simultaneity is detected during the initial set of single chamber pacing pulses. In other words, if simultaneity is detected, the ICD controller initiates the dual chamber ATP pacing and applies discrimination rules based on the heart's response to the dual chamber pacing. If simultaneity is not detected, the ICD selects tachycardia discrimination rules relating to the heart's response to the single chamber pacing. The selected tachycardia discrimination rules may involve an analysis of the cycle length of Asense events 106 during pacing, and the patterns and/or intervals of final Asense events 134 during pacing and the first Asense event 136 after pacing is terminated, and final pacing pulse 130 and the subsequent first Vsense event 132.

Figure 7:
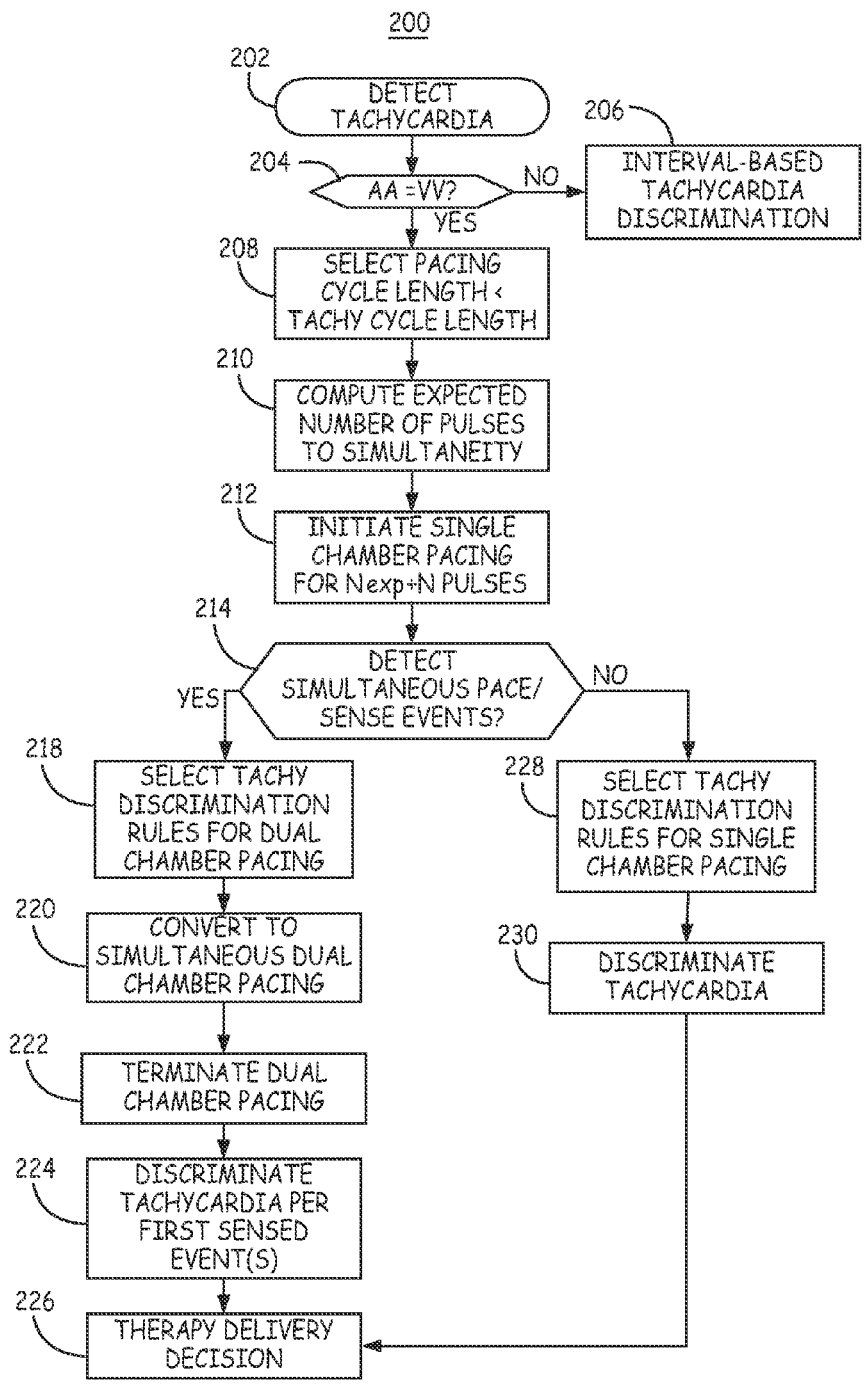
FIG. 7 is a flow chart of a method for delivering ATP.

FIG. 7 is a flow chart of a method for delivering ATP. Flow chart 200 is intended to illustrate the functional operation of the device, and should not be construed as reflective of a specific form of software or hardware necessary to practice the methods described. It is believed that the particular form of software will be determined primarily by the particular system architecture employed in the device and by the particular detection and therapy delivery methodologies employed by the device. Providing software to accomplish the described functionality in the context of any modern cardiac medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Method 200 is initiated upon detecting tachycardia at block 202. A determination may be made at block 204 as to whether the Asense cycle lengths and the Vsense cycle lengths are approximately equal. e.g., within 30 ms of each other. If not, interval and/or pattern based tachycardia discrimination methods may be used at block 206 to classify the tachycardia, e.g. as SVT, VT or dual tachycardia. Examples of pattern-based methods for tachycardia discrimination are generally disclosed in the above-referenced '186 Olson patent.

If the Asense cycle lengths and the Vsense cycle lengths are substantially equal, interval or pattern based discrimination methods may be indiscriminate. ATP is initiated to allow discrimination methods to be performed based on the heart's response to ATP. The ATP may additionally serve to terminate the tachycardia. As described above, ATP is initiated with a set of single chamber pacing pulses to avoid delivering a pacing pulse in either of the chambers during the vulnerable zone.

At block 208, a pacing cycle length is selected to be less than the tachycardia cycle length. The pacing cycle length can be applied to single chamber pacing pulses delivered in either the atria or the ventricles. The pacing cycle length may be set as a percentage of the tachycardia cycle length.

The chamber to be paced (atrium or ventricle) can be selected based on clinician preference or by default as always the atrium or always the ventricle. Alternatively, the paced chamber may be selected automatically by the IMD. The IMD may select the paced chamber as the chamber expected to be the origin of the tachycardia. The expected chamber of origin may be identified based on detected arrhythmia precursors, event patterns or intervals, or morphological analysis. In one embodiment, the variability of the tachycardia cycle length in each chamber may be evaluated, e.g. over a predetermined number of cycles, and the chamber exhibiting the least cycle length variability is selected as the paced chamber.

The expected number of pacing pulses required to reach simultaneity between a single chamber pacing pulse and a sensed depolarization in the non-paced chamber is computed at block 210. The computation at block 210 uses the selected pacing cycle length, the measured tachycardia cycle length prior to initiating ATP and a measured interval between a sensed atrial and a sensed ventricular event (sensed AV interval or sensed VA interval prior to initiating ATP pacing).

At block 212, the single chamber pacing pulses are delivered in the selected chamber, i.e. in only one or both atrial chambers or in only one or both ventricular chambers but not in both an atrial and a ventricular chamber. A maximum number of single chamber pacing cycles may be delivered at block 212 based on the expected number of required pacing pulses (Nexp). Exactly the computed number of required pacing pulses or a selected number greater than the computed number of required pacing pulses to reach simultaneity may be delivered.

At block 214, sensing is performed in the non-paced chamber during single chamber pacing to determine if simultaneity between a sensed depolarization in the non-paced chamber and one of the single chamber pacing pulses is detected. If all of the specified number of single chamber pacing pulses are delivered without detecting simultaneity, the ICD controller withholds the delivering of dual chamber ATP.

At block 228, the ICD controller selects tachycardia discrimination rules relating to the heart's response to single chamber ATP in response to not detecting simultaneity. At block 230, the selected tachycardia discrimination rules will be applied to sensed event intervals and/or sensed event patterns detected during and/or immediately after the single chamber pacing in order to discriminate the detected tachycardia as SVT, VT or a dual tachycardia. Tachycardia discrimination rules applicable to a single-chamber pacing response and used during the analysis performed at block 230 may correspond to any of the methods described in the above-incorporated references.

Referring to again to decision block 214, if simultaneity between a sensed event in the non-paced chamber and a single chamber pacing pulse is detected, the ICD controller selects tachycardia discrimination rules relating to the heart's response to dual chamber ATP at block 218 and immediately converts the single chamber ATP to simultaneous dual chamber ATP at block 220. This conversion to dual chamber pacing allows dual chamber ATP to be initiated with a reduced likelihood of pacing either chamber during the vulnerable zone. Pacing pulses are now delivered simultaneously in both atrial and ventricular chambers, e.g., at a 0 ms AVI and at the same pacing cycle length. The pacing cycle length during dual chamber pacing is less than the originally-detected tachycardia cycle length measured prior to initiating ATP and is generally equal to the pacing cycle length during single chamber pacing but is not limited to being equal. For example, the pacing cycle length could be adjusted to be a shorter pacing cycle length during dual chamber pacing than during single chamber pacing.

The tachycardia discrimination rules selected at block 218 in response to detecting simultaneity at block 214 allow the heart's response to the dual chamber ATP to be analyzed for discriminating SVT and VT. The dual chamber pacing is terminated at block 222, for example after a predetermined number of pacing cycles or pulses, such as 10 pacing pulses. Discrimination of the tachycardia is performed by applying the selected rules and using at least the first sensed event occurring after ATP termination at block 224. Tachycardia discrimination methods performed at block 224 may involve identifying only the first sensed event following termination as generally described in the above-incorporated Saba patent, or detecting two or more sensed events and evaluating event intervals and/or event patterns following ATP termination. In one embodiment, the tachycardia chamber of origin is identified as the chamber in which the first sensed event occurs following termination of dual chamber ATP.

At block 226, a therapy delivery decision is made based on the results of the discrimination analysis performed at block 224 or block 230. The therapy decision may be, for example, to withhold a therapy, select a tiered therapy, or deliver other anti-tachycardia pacing regimes or a cardioversion/defibrillation shock. For example, a ventricular therapy may be withheld in response to determining the tachycardia is SVT. The therapy decision may also include withholding a therapy due to a determination that the tachycardia has been terminated by the ATP. When a VT is detected, appropriate therapy may be delivered, which may include additional ATP and/or shocks, e.g. delivered in a tiered therapy scheme.

Thus, a cardiac medical device and associated method for controlling the delivering a cardiac therapy have been presented in the foregoing description with reference to specific embodiments. It is appreciated that various modifications to the referenced embodiments may be made without departing from the scope of the disclosure as set forth in the following claims.

The invention claimed is:

1. A cardiac medical device for delivering anti-tachycardia pacing, comprising:
   a plurality of electrodes implantable within a patient to sense cardiac signals in an atrium and in a ventricle and to deliver therapy in the atrium and in the ventricle; and
   a controller electrically connected to the plurality of electrodes, the controller detecting a tachycardia from the cardiac signals and controlling delivery of a plurality of pacing pulses via the plurality of electrodes in response to detection of the tachycardia,
   the plurality of pacing pulses comprising an initial set of single chamber pacing pulses delivered in a single one of the atrium and the ventricle, the other one of the atrium and the ventricle being a non-paced chamber during the initial set of single chamber pacing pulses,
   the single chamber pacing pulses delivered at a rate faster than a rate of the detected tachycardia,
   the controller detecting whether a simultaneity between a sensed event in the non-paced chamber and one of the single chamber pacing pulses occurs and delivering a next set of dual chamber pacing pulses delivered in both the atrium and the ventricle in response to detecting the simultaneity.

2. The cardiac medical device of claim 1, wherein the dual chamber pacing pulses are delivered at a rate faster than the detected tachycardia.

3. The cardiac medical device of claim 1, wherein the dual chamber pacing pulses are delivered simultaneously in the atrium and the ventricle.

4. The cardiac medical device of claim 1 wherein the controller computes an expected number of single chamber pacing pulses required to achieve the simultaneity.

5. The cardiac medical device of claim 4 wherein the controller sets a maximum number of pacing pulses in the initial set of single chamber pacing pulses in response to the computed expected number of single chamber pacing pulses.

6. The cardiac medical device of claim 5 wherein the controller withholds the next set of dual chamber pacing pulses in response to delivering the maximum number of single chamber pacing pulses without detecting simultaneity between a sensed event in the non-paced chamber and one of the single chamber pacing pulses.

7. The cardiac medical device of claim 6 wherein the controller selects tachycardia discrimination rules in response to whether simultaneity is detected during the initial set of single chamber pacing pulses and applies the selected rules to discriminate the detected tachycardia.

8. The cardiac medical device of claim 1 wherein the controller selects the single one of the atrium and the ventricle to receive the single chamber pacing pulses in response to the cardiac signals.

9. The cardiac medical device of claim 8 wherein selecting the single one of the atrium and the ventricle comprises determining a lowest tachycardia cycle length variability.

10. A method for delivering anti-tachycardia pacing, comprising:
    sensing cardiac signals in an atrium and in a ventricle;
    detecting tachycardia from the cardiac signals;
    delivering a plurality of pacing pulses in response to detecting the tachycardia, the plurality of pacing pulses comprising an initial set of single chamber pacing pulses delivered in a single one of the atrium and the ventricle, the other one of the atrium and the ventricle being a non-paced chamber during the initial set of single chamber pacing pulses, the single chamber pacing pulses delivered at a rate faster than a rate of the detected tachycardia; and
    detecting whether a simultaneity between a sensed event in the non-paced chamber and one of the single chamber pacing pulses occurs; and
    delivering a next set of dual chamber pacing pulses delivered in both the atrium and the ventricle in response to detecting the simultaneity.

11. The method of claim 10, wherein the dual chamber pacing pulses are delivered at a rate faster than the detected tachycardia.

12. The method of claim 10, wherein the dual chamber pacing pulses are delivered simultaneously in the atrium and the ventricle.

13. The method of claim 10, further comprising computing an expected number of single chamber pacing pulses required to achieve the simultaneity.

14. The method of claim 13 further comprising setting a maximum number of pacing pulses in the initial set of single chamber pacing pulses in response to the computed expected number of single chamber pacing pulses.

15. The method of claim 14 further comprising withholding the next set of dual chamber pacing pulses in response to delivering the maximum number of single chamber pacing pulses without detecting simultaneity between a sensed event in the non-paced chamber and one of the single chamber pacing pulses.

16. The method of claim 15 further comprising selecting tachycardia discrimination rules in response to whether simultaneity is detected during the initial set of single chamber pacing pulses; and
    applying the selected rules to discriminate the detected tachycardia.

17. The method of claim 10, further comprising selecting a single one of the atrium and the ventricle for receiving the initial set of single chamber pacing pulses in response to the cardiac signals.

18. The method of claim 17 wherein selecting a single one of the atrium and the ventricle comprises determining a lowest tachycardia cycle length variability.

19. A non-transitory computer-readable medium programmed with instructions for delivering anti-tachycardia pacing, the medium comprising instructions for causing a programmable processor to:
    sense cardiac signals in an atrium and in a ventricle;
    detect tachycardia from the cardiac signals;
    deliver a plurality of pacing pulses in response to detecting the tachycardia, the plurality of pacing pulses comprising an initial set of single chamber pacing pulses delivered in a single one of the atrium and the ventricle, the other one of the atrium and the ventricle being a non-paced chamber during the initial set of single chamber pacing pulses, the single chamber pacing pulses delivered at a rate faster than a rate of the detected tachycardia; and
    detecting whether a simultaneity between a sensed event in the non-paced chamber and one of the single chamber pacing pulses occurs; and
    delivering a next set of dual chamber pacing pulses delivered in both the atrium and the ventricle in response to detecting the simultaneity.

* * * * *